(12) United States Patent
Creelman et al.

(10) Patent No.: US 11,964,278 B2
(45) Date of Patent: Apr. 23, 2024

(54) MICROFLUIDIC CHIP, SYSTEMS, AND METHODS FOR CAPTURING OF ENVIRONMENTAL DNA

(71) Applicant: Dartmouth Ocean Technologies Inc., Dartmouth (CA)

(72) Inventors: Joshua Johannes Creelman, Halifax (CA); Edward Arthur Luy, Halifax (CA); Gabryelle Cecile Henderson Beland, Halifax (CA); Sean Christopher Morgan, Halifax (CA); Marie Evelyn Julie LaRoche, Halifax (CA); Mahtab Tavasoli, Bedford (CA); Robert Gerald Beiko, Upper Sackville (CA); Roger Edmund Race, Dartmouth, MA (US); Arnold Furlong, Fall River (CA); Vincent Joseph Sieben, Bedford (CA)

(73) Assignee: DARTMOUTH OCEAN TECHNOLOGIES INC., Dartmouth (CA)

( * ) Notice: Subject to any disclaimer, the term of this patent is extended or adjusted under 35 U.S.C. 154(b) by 232 days.

(21) Appl. No.: 17/468,986

(22) Filed: Sep. 8, 2021

(65) Prior Publication Data
US 2022/0072547 A1   Mar. 10, 2022

Related U.S. Application Data

(60) Provisional application No. 63/075,548, filed on Sep. 8, 2020.

(51) Int. Cl.
*G01N 33/68* (2006.01)
*A01N 1/02* (2006.01)
(Continued)

(52) U.S. Cl.
CPC ... *B01L 3/502753* (2013.01); *B01L 3/502715* (2013.01); *B01L 3/502761* (2013.01);
(Continued)

(58) Field of Classification Search
CPC ........ B01L 3/502753; B01L 3/502715; B01L 3/502761; B01L 2200/0631;
(Continued)

(56) References Cited

U.S. PATENT DOCUMENTS

2005/0250199 A1* 11/2005 Anderson ............. B01L 3/5027
435/288.5
2015/0136602 A1* 5/2015 Jovanovich ...... G01N 27/44721
204/601
2017/0198329 A1* 7/2017 Ayyub ............... G01N 33/6893

FOREIGN PATENT DOCUMENTS

WO   WO-2011118873 A1 *  9/2011  ......... G01N 21/6486

* cited by examiner

*Primary Examiner* — Jennifer Wecker
*Assistant Examiner* — Oyeleye Alexander Alabi
(74) *Attorney, Agent, or Firm* — Pearne & Gordon LLP

(57) ABSTRACT

A microfluidic lab-on-a-chip (LOC) device, microfluidic systems, and associated methodology are described that allow for intelligently collecting environmental DNA (eDNA) and their associated metadata. Optical spectroscopy is integrated with filtration membranes on the microfluidic device. The microfluidic LOC device and systems can be used for selectively capturing targeted species based on optical characteristics and for recording relevant metadata on eDNA acquired by the filtration membranes.

24 Claims, 12 Drawing Sheets

(51) Int. Cl.
*B01L 3/00* (2006.01)
*C07C 309/65* (2006.01)
*C07C 309/73* (2006.01)
*F04B 43/12* (2006.01)
*G01N 1/40* (2006.01)
*G01N 21/33* (2006.01)
*G01N 21/64* (2006.01)
*G01N 33/52* (2006.01)
*G01N 35/10* (2006.01)

(52) U.S. Cl.
CPC .................. *B01L 2200/0631* (2013.01); *B01L 2300/0663* (2013.01); *B01L 2300/0681* (2013.01); *B01L 2300/0803* (2013.01); *B01L 2300/0867* (2013.01); *G01N 21/64* (2013.01)

(58) Field of Classification Search
CPC ..... B01L 2300/0663; B01L 2300/0681; B01L 2300/0803; B01L 2300/0867; B01L 2300/0861; B01L 2400/0487; G01N 21/64; G01N 1/12; G01N 2001/1012; G01N 33/1893
See application file for complete search history.

11,964,278 B2

MICROFLUIDIC CHIP, SYSTEMS, AND METHODS FOR CAPTURING OF ENVIRONMENTAL DNA

CROSS-REFERENCE TO RELATED APPLICATIONS

The present application claims priority to U.S. Provisional Patent Application No. 63/075,548, filed Sep. 8, 2020, the entire contents of which is incorporated herein by reference for all purposes.

TECHNICAL FIELD

The present disclosure relates to capturing environmental DNA and in particular to collection and storage of environmental DNA samples.

BACKGROUND

Environmental DNA (eDNA) is being used to augment or replace traditional ways of assessing biodiversity. Key amongst its strengths are the ability to identify organisms that would otherwise be undetectable due to their small size or rarity, its ability to differentiate groups of interest (e.g., by identifying organisms of interest that are impossible to visually distinguish), and the potential to give a more comprehensive picture of biodiversity. eDNA can serve as an early-warning system for environmental change: for example, by identifying rapid shifts in toxic microbial species. Current methods for eDNA analysis automate the identification process through the use of DNA sequencing and bioinformatics tools, but collection of samples from the environment remains a laborious process. Typical eDNA sampling techniques remain labour-intensive, with the need for site visits, manual collection of samples in sufficient volumes using sterile equipment, and stable transportation of the samples to the lab for DNA extraction and analysis.

Accordingly, devices, systems, and methods that enable eDNA sampling remains highly desirable.

BRIEF DESCRIPTION OF THE DRAWINGS

Features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
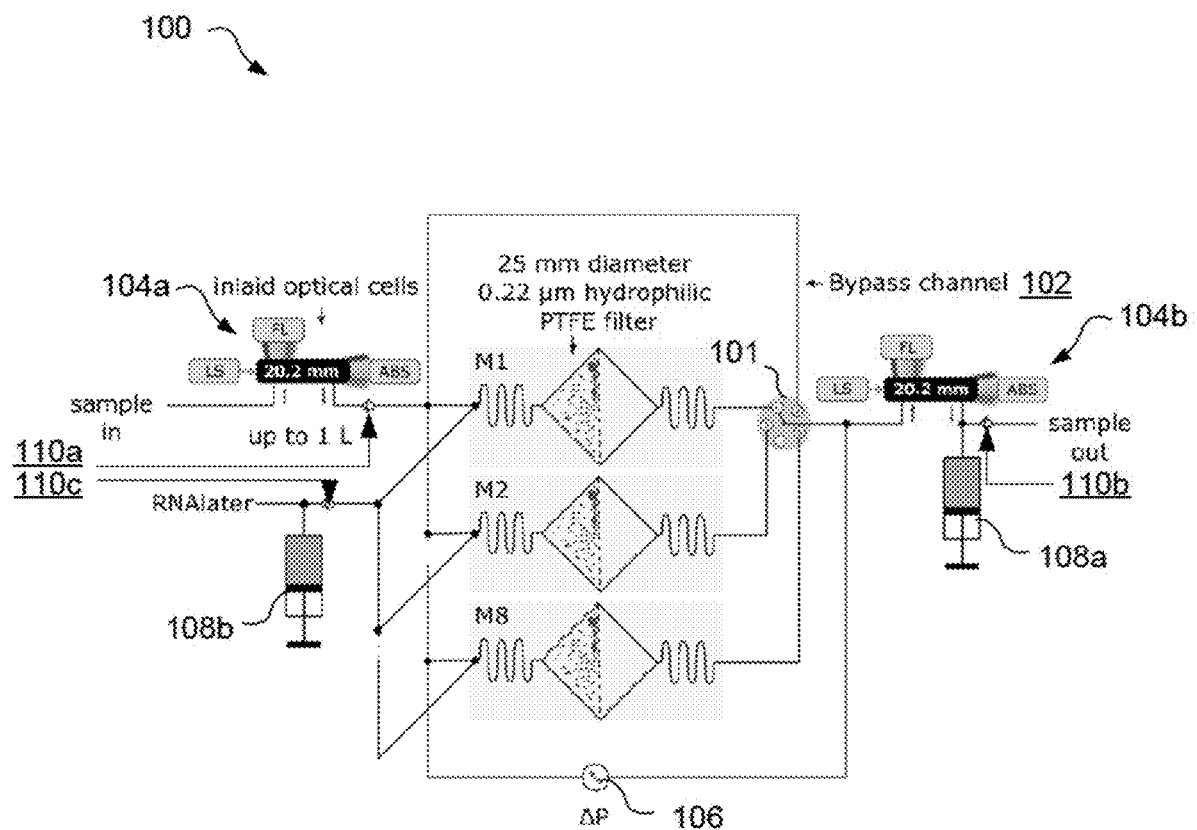
FIG. 1 shows a fluid schematic of a microfluidic sampling system.

In accordance with one aspect of the present disclosure, a microfluidic system is disclosed, comprising: an environmental sample inlet port; a preservative reagent inlet port; a waste outlet port; one or more discrete filter membranes for particle concentration; at least one fluid access port that permits control of the sample fluid stream through a selected filter membrane; at least one optical flow cell that enables at least one of light microscopy, fluorescence spectroscopy, light attenuation measurements, and scattered light intensity measurements, situated before the one or more filter membranes to interrogate the incoming sample fluid stream; and at least one bypass channel to enable disposal of the incoming fluid sample stream and avoid capturing suspended microbes and/or particles on a filter membrane.

In some aspects, the microfluidic system comprises a microfluidic chip having a plurality of layers, comprising: an upper layer defining the environmental sample inlet port, the preservative reagent inlet port, the waste outlet port, and in fluid communication with at least one intermediate layer; an intermediate layer in fluidic communication with the one or more filter membranes; and a lower layer in fluid communication with the intermediate layer, incorporating the at least one fluid access port, and the at least one optical flow cell in optical communication with an instrumentation housing.

In some aspects, the at least one optical cell comprises at least one of an absorbance measurement channel and a fluorescence measurement chamber.

In some aspects the microfluidic system further comprises at least one photodetector that detects chlorophyll and/or phycocyanin absorbance or fluorescence changes.

In some aspects, optical measurements are used to determine redirection of sample away from a filter via the bypass channel.

In some aspects, optical measurements are used to determine whether sufficient gene copy numbers per liter filtered have been collected on a targeted filter by estimating biomass through at least one correlation factor.

In some aspects, the microfluidic system further comprises a pressure sensor, and wherein pressure measurements are used to determine sufficient sample concentration and/or biomass collection on the targeted filter, and wherein sample fluid volume filtered through each membrane is tracked and recorded to determine gene copy numbers per liter.

In some aspects the microfluidic system comprises a plurality of filter membranes, wherein a branched multiplexing channel links the sample inlet port to the plurality of filter membranes; and fluid flow through a respective filter membrane is enabled by a selector valve on the outlet side of each filter membrane, enabling selective capture of particles and microbes in the fluid stream on a desired membrane.

In some aspects, a meandering channel extends behind the one or more filter membranes for providing volume capacity to avoid preservative from entering the waste outlet port.

In some aspects the microfluidic system further comprises a photodetector and a processing unit configured to receive data from the photodetector for analyzing the detected changes to enable intelligent fluid routing.

In some aspects the microfluidic system further comprises a photodetector and a processing unit configured to receive data from the photodetectors for analyzing the sample's fluorescence spectral data to determine the presence of phytoplankton and cyanobacteria.

In some aspects the microfluidic system further comprises multiple light emitting diode sources, configured to be activated sequentially to identify and record at least one of fluorescence and absorbance spectral signatures.

In some aspects, the environmental sample inlet port is configured to receive the sample fluid from a lift pump on a towed-body to enable capture of eDNA samples topside on a ship-based system, while the collection point is submerged.

In some aspects the microfluidic system further comprises a magnetic retention of the microfluidic chip layers to enable rapid membrane removal and/or insertion.

In some aspects the microfluidic system further comprises a second optical flow cell situated after the one or more filter membranes for acquiring optical data of the permeate or post-filtration.

In some aspects, signals from a first optical flow cell of the at least one optical flow cell are compared to signals from the second optical flow cell to detect capture efficiency; and wherein the signals from the first and second optical flow cells, before and after filtration, enable detection of membrane failures, and quantification of membrane capture efficiency as relates to pore-size and particle composition in the fluid stream, and wherein the microfluidic system further comprises a processing unit and a memory storing non-transitory computer-readable instructions that, when executed by the processing unit causes the processing unit to calibrate the first optical flow cell data to the second optical flow cell data using the bypass channel.

In some aspects the microfluidic system further comprises forward scatter and side capture ports at multiple angles for particle sizing.

In some aspects, at least one of a fluorescence signal threshold and an attenuation signal threshold is used to trigger capture on a filter membrane with appropriate time stamp.

In some aspects, time-series fluorescence and absorbance spectra are used to determine sample concentration, or gene copy numbers per liter filtered, collected on a targeted filter by estimating biomass through at least one correlation factor.

In some aspects, the microfluidic system is configured to interface with a bench-top apparatus for subsequent eDNA extraction and analysis procedures.

In some aspects, the at least one optical flow cells are used to capture eluted pigment spectral data during DNA extraction to correlate to biomass captured.

In some aspects, the downstream analysis takes the DNA product or template to determine the presence of genes that are characteristic of certain species, including toxin genes.

In some aspects, a volume threshold, a pressure threshold, an optical threshold, and/or any combination thereof are user-specified to determine when to initiate and terminate the filtration of the sample fluid stream on a particular membrane.

In accordance with another aspect of the present disclosure, a method is disclosed, comprising: deploying a microfluidic system on a submersible instrument, the microfluidic system comprising: an environmental sample inlet port; a preservative reagent inlet port; a waste outlet port; one or more discrete filter membranes for particle concentration; at least one fluid access port that permits control of the sample fluid stream through a selected filter membrane; at least one optical observation flow cell that enables at least one of light microscopy, fluorescence spectroscopy, light attenuation measurements, and scattered light intensity measurements, situated before the one or more filter membranes to interrogate the incoming sample fluid stream; and at least one bypass channel to enable disposal of the incoming fluid sample stream and avoid capturing suspended microbes and/or particles on a filter membrane; collecting a sample on the one or more filter membranes; conveying acquired data to operators via at least one of memory mode or wireless linkages; retrieving the microfluidic system upon collecting sufficient biomass; and connecting the microfluidic system to a benchtop stand-alone system for performing eDNA extraction procedures.

In some aspects, optical data is shared with a deployment platform's autonomy framework for intelligent sampling that can be coordinated with the platform's georeferenced location, and further comprising performing adaptive sampling where the real-time measured optical data and a user-specified threshold are communicated to an autonomous water craft or vehicle that performs navigation and localization for automated eDNA water collection, including searching for the absence or presence of specific spectral signatures such as increases in phytoplankton.

There are several applications of eDNA technology, which may include, for example, applications as described below.

One example application is monitoring of threatened species in river ecosystems. Atlantic salmon stocks have declined drastically over the last 50 years, with 2019 numbers among the lowest observed during this period, and this commercially important species has now disappeared from many river systems. eDNA may be used to find evidence of salmon presence in rivers where salmon are either rare or extirpated, and to differentiate populations of salmon that play different ecological roles. A microfluidic chip eDNA sampler as described herein can be deployed as a bottom mounted or vertical profiling sensor. Based on the choice and number of probes used, the sensor can be used to monitor for any type of salmon, or one or more target subspecies or populations. A bottom-mounted sensor can be deployed at a variety of locations along a known salmon spawning river or a series of vertical profiling robots can house the eDNA sensor and carry out vertical profiles (surface to river bottom) over a distance as the profiler flows toward the river outflow into the ocean. During the course of these measurements the eDNA sensor data can be logged internally of transmitted via a variety of communications channels including cell phone, satellite coms, or VHS.

Another example application is identification of microorganisms associated with corrosion in oil pipelines. Many species of bacteria are known to contribute to microbiologically influenced corrosion (MIC) of oil pipelines. These microorganisms often develop resistance to the biocides that are used to treat them. Monitoring oil pipeline flows for evidence of these organisms and resistance traits can serve as an early indicator of MIC, and guide the choice of remediation approach.

Another example application is environmental site assessment survey for fisheries, oceanography, aquaculture site selection, tourism industry. Scientists and environmental consulting companies often need to collect eDNA samples remotely for several months without the ability to retrieve the samplers. The samples must be preserved in situ to maintain their integrity until analysis in the laboratory. Application of the eDNA sampler with a high throughput sampling capacity (e.g. up to 72 samples within a period of several months) and the ability to a targeted sampling regime as a function of environmental conditions is advantageous.

Another example application is surveillance for invasive species related to ship and submarine routes. The addition of an eDNA sampler would be strategic for the detection of the eDNA of sloughed off alien invasive species of algae that are typically found in the geographic locations of adversaries. An eDNA sampler would assist friendly forces seeking to detect adversary fleet movements and locations.

Another example application is complementing photograph and video data acquisition systems. For example, the Baited Remote Underwater Video Systems (BRUVS) are remote systems used to document the sea life and ecology of a site on the sea floor. The technology is used extensively in the shallow littoral waters of countries. An eDNA sampler can be deployed in concert with BRUVS technology and water bottle collection to validate data sampling related to fish and crustaceans feeding on baited systems.

Another example application is integration with long-term observation networks. For example, providing bio-monitoring as part of the Environment Canada CABIN project. Comprehensive datasets with other biogeochemical sensors (e.g. phosphate, nitrate) show long-term anthropogenetic induced shifts.

Another example application is health monitoring through water treatment facilities. Pathogenic species of interest such as *C. difficile, E. coli, Salmonella*, and *Pseudomonas*, can be detected in wastewater streams emanating from facilities that house vulnerable individuals (e.g., assisted-care facilities, hospitals). Targeting of species-specific marker genes or genes conferring antimicrobial resistance can be used to identify outbreaks and rapidly respond to potential health risks.

Yet another example application is harmful algal blooms (HABs) detection. HABs are notorious for fish kills, food poisoning (e.g. shellfish) and public health issues arising from contaminated beaches and drinking water. It is estimated that in the U.S. alone, $2.2-$4.6 billion dollars are lost annually due to eutrophication and freshwater HABs. Aquaculture is particularly susceptible to HAB events, as the capital investment in the remote farm currently has no early warning system for prevention or mitigation measures.

Each of these domains of eDNA technology application has unique challenges associated with sample collection and preservation,. which would benefit from devices that can perform in situ collection and storage of environmental DNA samples for later analysis.

Looking at HABs, simple measures to keep the stock safe, like protective curtain barriers, bubble curtains, moving the fish or harvesting early, could be enacted if HABs were detected with sufficient time to respond.

Fluorometers are commercially available to detect key HAB pigments, but this approach is fundamentally not able to discriminate toxic from non-toxic plankton. Therefore, real-time and accurate detection of the toxic species triggering the HAB event remains unsolved. Genetic analysis is one of the only sure-fire ways to identify the toxin producing species.

In accordance with the present disclosure, a microfluidic lab-on-a-chip (LOC) device, microfluidic systems, and associated methodology are described to intelligently collect environmental DNA (eDNA) and their associated metadata (e.g. pigment fluorescence). Optical spectroscopy is integrated with filtration membranes on the same device. The microfluidic LOC device and microfluidic systems can be used for selectively capturing targeted species based on optical characteristics and for recording relevant metadata on eDNA acquired by a filtration system. The present invention has numerous applications, such as the early detection of harmful algal blooms (HABs) and other applications such as those described above. For instance, simultaneous absorbance and fluorescence of chlorophyll and phycocyanin may be used for detecting onsets of HABs and determination of potential toxins involved because of changes in microalgae and cyanobacteria. Once a critical optical threshold is observed, the device may be configured to reroute fluid to capture the environmental DNA on a filtration membrane for further genetic assay to determine for example the presence of toxin genes or a HAB species. The device and methods are applicable to any and multiple eDNA targets (non-exhaustively to the detection of any marker gene or genetic barcode that identifies the presence of a particular biochemical pathway, pathogen, invasive or endangered species, or as communicated by the client). The LOC system can detect the early onset of a HAB using optical spectroscopy and can use this information to determine when to initiate and terminate the filtration of cells on the membrane as a function of the cell biomass in the natural environment in real time. Multiple optical spectroscopy flow cells on the same device may be used to enable active and smart filtration to concentrate targeted samples on the integral membranes and they provide quality control for capture efficiency on the membrane. Membrane retained material may be time-stamped with optical data, permitting correlation to the downstream genetic analysis for further identification of toxin-producing species.

Embodiments are described below, by way of example only, with reference to FIGS. 1-12.

FIG. 1 shows a fluid schematic of a microfluidic sampling system 100. The microfluidic sampling system comprises one or more discrete filter membranes for particle concentration, and in this embodiment the microfluidic sampling system 100 has eight membrane filters (M1, M2, . . . M8) multiplexed with a selector valve 101, but more or less membrane filters may be present. The membrane filters M1-M8 may for example be a 25 mm diameter, 0.22 µm hydrophilic PTFE filter. The selector valve 101 also is connected to a bypass channel 102 which bypasses the membrane filters M1-M8. The microfluidic sampling system 100 comprises two optical flow cells 104a and 104b, which may each be outfitted with two LEDs centered 430 nm and 605 nm (~15 nm FWHM), and each able to measure both fluorescence emission at ~660-680 nm and absorbance at the respective wavelengths; however the acquisition of multiple spectral ranges is possible with different LEDs, filters and detectors. The microfluidic sampling system 100 further comprises a pressure sensor 106 which is configured to measure the transmembrane pressure, such that pressure can be measured across any given membrane depending on the state of the selector valve 101. Further, the microfluidic sampling system 100 comprises two syringe pumps 108a and 108b, a first syringe pump 108a which flows sample through the system and a second syringe pump 108b which injects preservative onto a given membrane. The microfluidic sampling system 100 may also comprise three check valves ensuring no cross-contamination during fluid flow.

Each membrane filter M1-M8 is configured to collect and concentrate separate samples. The bypass channel 102 can be used in conjunction with the optical measurements to intelligently control what samples are retained on each membrane. For instance, the first fluorometer/optical flow cell 104a before the membranes can be used to determine that sufficient biomass sample has been collected on a membrane. Similarly, the second fluorometer/optical flow cell 104b can detect any sample that has breached a membrane, indicating reduced collection efficiency or a membrane tear or failure. Pressure profiles over time can also be used to track sample accumulation and volume filtered on the membrane as fluid is collected and pumped on the targeted membrane. A first check valve 110a may be near the sample intake (sample in) to ensure preservative is not dispensed through the intake. A second check valve 110b may be near the outtake (sample out) to prevent waste from the environment entering the system. A third check valve 110c may be just after the preservative to ensure sample is not unintentionally introduced to preservative system.

Figure 2:
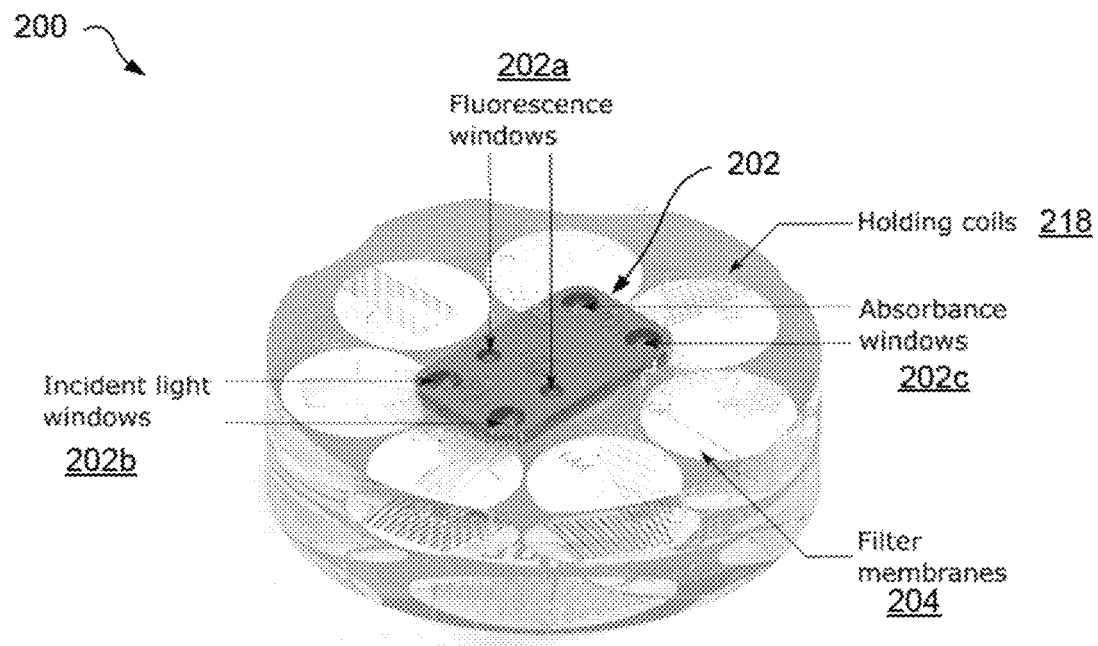
FIG. 2 shows a CAD rendering of one embodiment of a lab-on-chip microfluidic system.

FIG. 2 shows a CAD rendering of one embodiment of a lab-on-chip microfluidic system 200. The microfluidic sampling system as described in FIG. 1 may be provided on a chip comprised of a plurality of layers. FIG. 2 shows an isometric view of the optical coupling side or lower layer of the lab-on-chip microfluidic system. The integral opaque center piece is an optical measurement portion 202 of the chip. Seven filter membranes 204 can be clearly viewed from this angle, with one more membrane covered by the opaque optical measurement portion 202. The optical measurement portion 202 is for measuring absorbance and fluorescence as described in FIG. 1. There are six clear round windows that can be seen in the optical measurement portion 202. The smallest diameter windows 202a are where fluorescence is captured by a photodetector. To the left of the small windows are the ports 202b for coupling light to the optical system from external light sources. Incident light is directed by a prism inside these clear ports toward the smaller windows and subsequently the last window. The last windows (rightmost) 202c are where the absorbance or attenuated light is measured with a photodetector after traversing the length of optical flow cell. The absorbance ports also contain prisms which direct the light towards the detectors. There are also a number of ports in the LOC microfluidic system for the following: eight ports for the permeate side of the membranes 204 (M1-8 in FIG. 1), one port for the bypass channel (102 in FIG. 1), two for the transmembrane pressure sensor (106 in FIG. 1), two for an external check valve for the outtake, and a port connecting the second optical flow cell to the selector valve (101 in FIG. 1).

Figure 3:
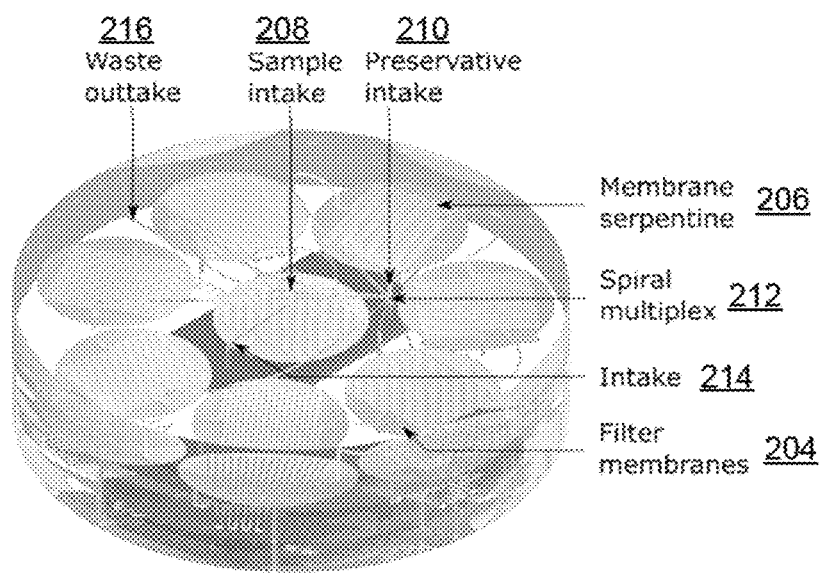
FIG. 3 shows the microfluidic chip shown in FIG. 2, as viewed from the top layer.

FIG. 3 shows the microfluidic chip shown in FIG. 2, as viewed from the opposite side of the device, or the top layer. All eight membranes 204 can now be seen clearly. Open-faced membrane serpentine channels 206 can also be seen mated to the filter membranes. The membrane serpentine channels 206 permit fluid communication with the membrane to maximize surface area while providing sufficient mechanical support. There are three ports on the displayed face. One port is for the environmental sample inlet port for sample intake 208 (sample in), which travels through an intake via channel 214 leading to the first optical flow cell input, to measure optical properties of the sample intake. Another port is a preservative reagent inlet port for preservative reagent intake 210. The preservative port and first optical flow cell output lead to a spiral patterned channel 212 for multiplexing and establishing fluid communication to all eight membranes 204. This spiral is a series of channels of equal length leading to the eight membrane's serpentines. A third port is a waste outlet port for waste outtake 216.

Figure 4:
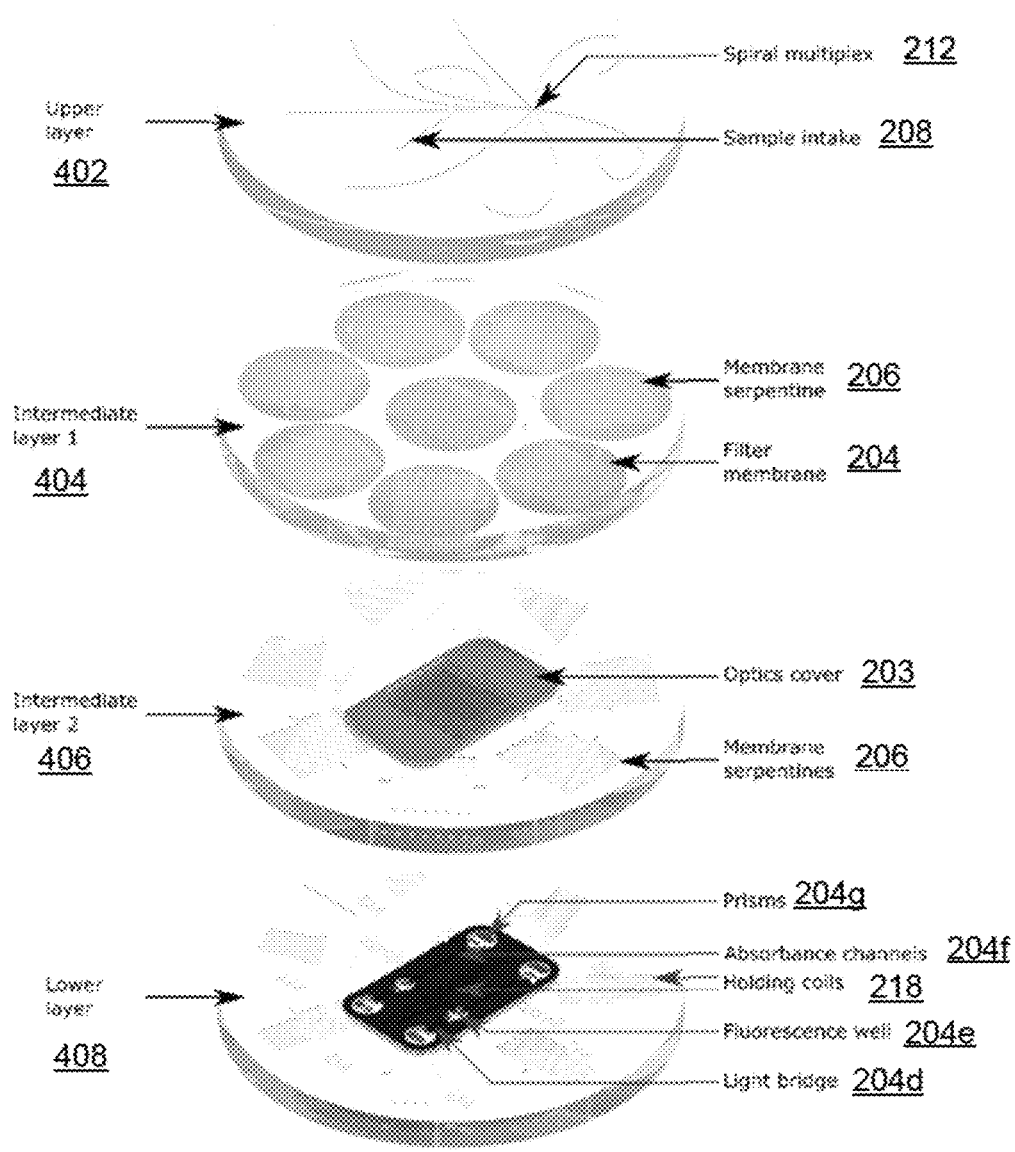
FIG. 4 shows an exploded view of the microfluidic chip shown in FIGS. 2 and 3.

FIG. 4 shows an exploded view of the microfluidic chip shown in FIGS. 2 and 3. This view clearly shows the internal microchannels, specifically, the channels in the opaque optical measurement section. Upper layer shows 402 the spiral multiplex channel 212 and the ports that provide sample intake and preservative intake. Intermediate layer 404, below the upper layer 402, shows the membrane filters 204 mated to the open-faced fluid coupling serpentine channels 206. Intermediate layer 406 shows the mirror open-faced serpentine channels 206 that couple to the filter membranes 204. These serpentine channels carry filtered sample or permeate to the lower layer. This intermediate layer 406 also contains a black inlay optics cover 203 which acts as a capping element for the optical flow cells, preventing ambient and stray light from reaching the photodetectors. Lower layer 408 contains the optical flow cells and holding coils 218. The holding coils 218 help to ensure when preservative is introduced that it does not reach the outlet, accomplished by providing excess channel volume on the permeate side of each membrane. The two optical flow cells are more distinct in the exploded view, showing the six ports comprising the two light source ports, the two absorbance measurement ports, and the two fluorescence measurement ports, as well as showing light bridge 204d, fluorescence well 204e, and absorbance channels 204f. Light directing prisms 204g are also viewable, showing that they are 45° cuts into the material.

Figure 5:
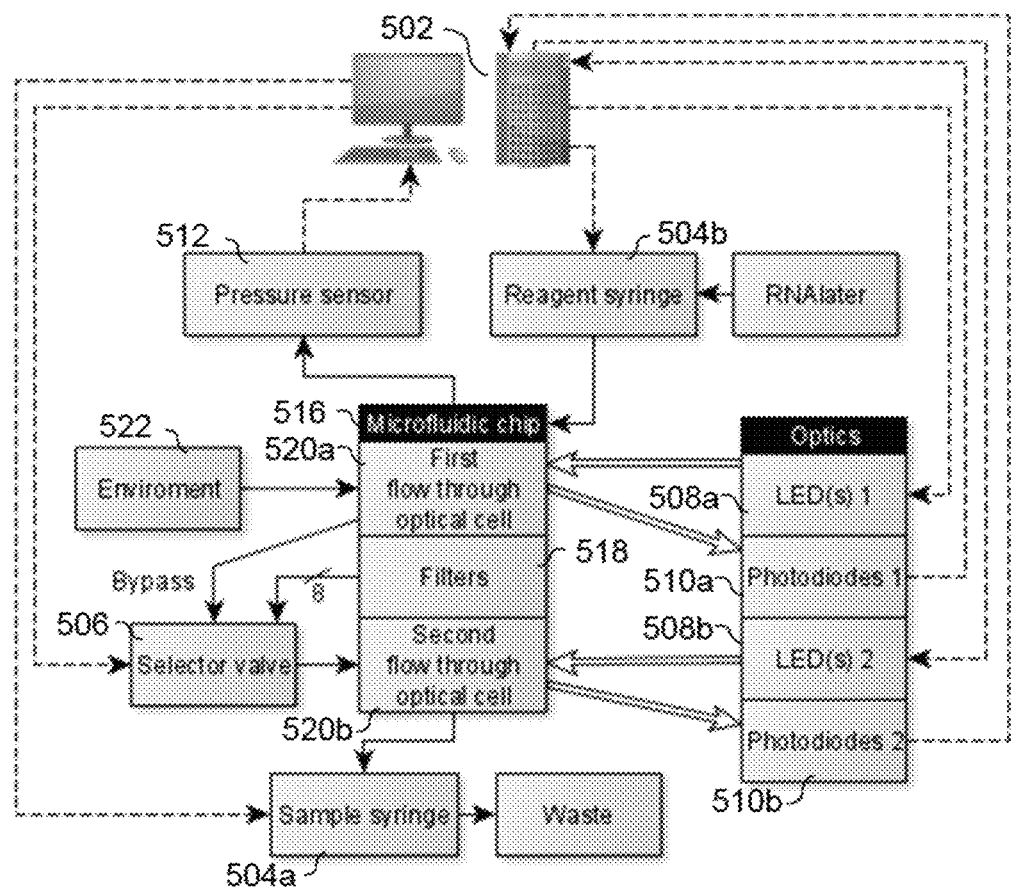
FIG. 5 shows an entity relationship diagram of the microfluidic system.

FIG. 5 is an entity relationship diagram of the microfluidic system. Solid lines indicate a fluidic connection, dashed lines indicate an electrical connection, and the parallel coupled lines indicate optical connections. A computer 502 is configured to send electrical signals controlling the two syringes 504a and 504b, the selector valve 506, and LEDs 508a and 508b. The computer 502 comprises a processing unit and a memory storing non-transitory computer-readable instructions which, when executed by the processing unit, configure the computer to perform various functionality as described herein. The computer 502 is configured to send electrical signals to the selector valve 506 for controlling a position of the selector valve. The computer 502 is configured to send electrical signals to the LEDs 508a-b for controlling an intensity of the LEDs, which also includes their off state. The computer 502 is configured to send electrical signals to the syringes 504a-b for controlling a position of the syringes. The computer 502 is also configured to receive signals comprising readings from the photodiodes 510a and 510b and pressure sensor 512. The readings can be recorded on the computer 502 to be further analyzed. The microfluidic chip 516 is comprised of one or more filters 518 and the two optical chambers 520a and 520b. The microfluidic chip 516 has fluidic connections with the two syringes 504a-b, the pressure sensor 512, and selector valve 506. The reagent syringe 504b injects fluid into the microfluidic chip 516 as indicated by the direction of the solid arrow. The sample syringe 504a draws fluid from the environment through the microfluidic chip 516. The selector valve 506 receives fluid from the filters 518 or first optical cell 520a and can send fluid to the second optical cell 520b, as indicated by the solid arrow. Fluid will pass from the environment 522, through the first optical cell 520a, then to one of the filters 518 or bypass channel depending on the selector valve's position. Transmembrane pressure is measured by the pressure sensor 512 through fluid access ports to the microfluidic chip 516. The LEDs 508a-b and detectors are held in an instrument housing and optically couple to the two optical flow cells 520a-b on the microfluidic chip 516.

Light is sent from the LEDs 508a-b to the optical cells 520a-b and light is received from the optical cells 520a-b by the photodiodes 510a-b.

Figure 6:
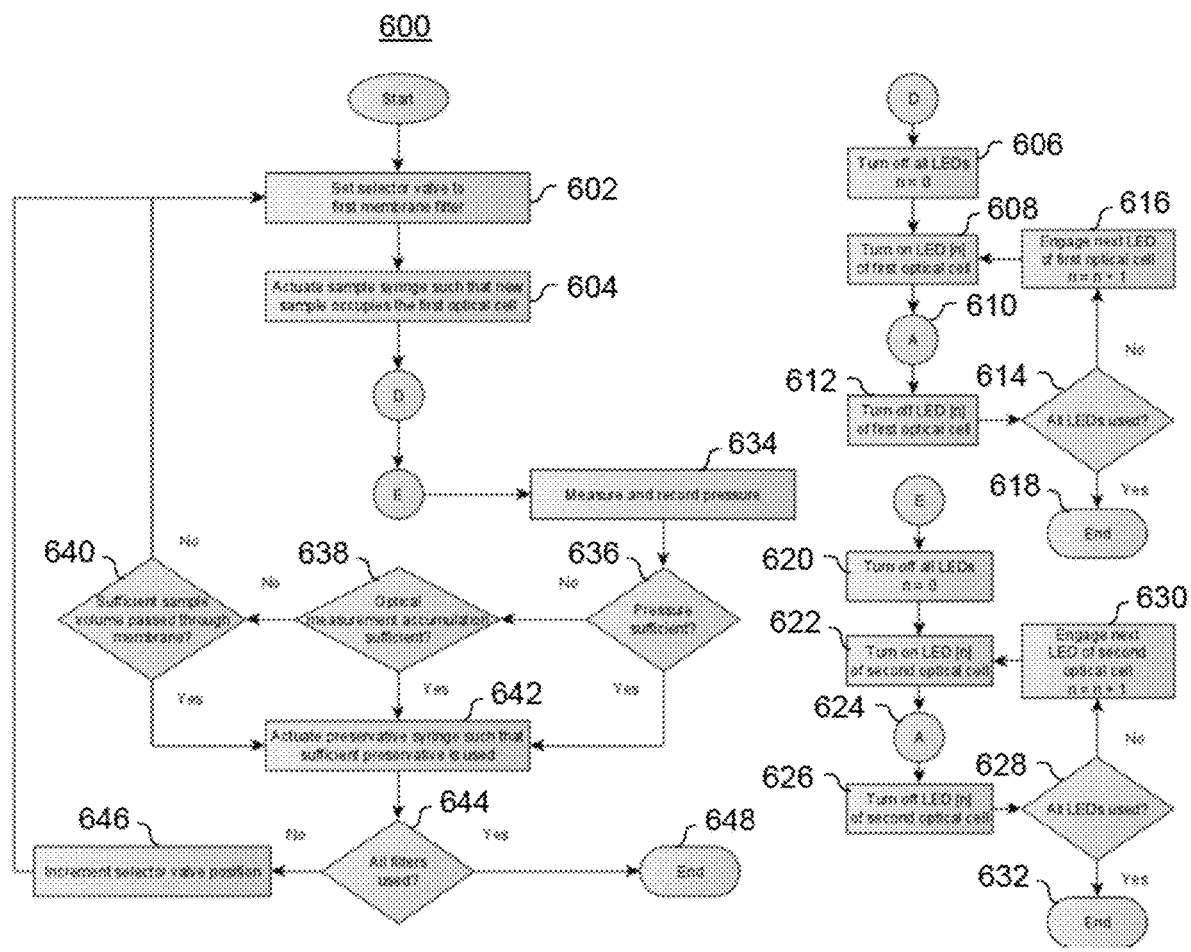
FIG. 6 shows a method for operating the microfluidic system.

FIG. 6 shows a method 600 for operating the microfluidic system. It begins with initialization of the selector valve and sets the selector valve to a first membrane filter (602), bridging the first membrane into the main sample fluid stream. The sample syringe is actuated (604) such that new sample is introduced to the first optical flow cell. In the described embodiment of the method for operating the microfluidic system, fluorescence and absorption measurements are acquired from this first optical flow cell using method "D". All LEDs are turned off and initially inactive (606). The optical measurement sequence commences by turning the first LED on (608) to engage the first LED, which corresponds to a desired target pigment in the sample fluid stream. In an example, there are two target pigments and thus two LEDs. For example, one LED1 may be intended for chlorophyll with a center wavelength of 430 nm and one LED2 may be intended for phycocyanin with a center wavelength of 605 nm. Once LED1 is engaged the photodetectors signals are recorded at "A" (610), which is described in more detail below with reference to FIG. 8. LED1 is turned off (612), a determination is made if all LEDs have been used (614), and in this example there are two LEDs so not all LEDs have been used (NO at 614). The next LED (LED2) is turned on (616) and the photodiode signals are recorded. The method continues until all LEDs have been used (YES at 614), at which point the method for the first optical cell ends (618).

The process is repeated for the second optical flow cell using method "E". All LEDs of the second optical flow cell are turned off (620). The optical measurement sequence commences by turning on the first LED (622) of the second optical cell. Once the first LED is engaged the photodetectors signals are recorded at "A" (624), which is described in more detail below with reference to FIG. 8. The first LED is turned off (626), and a determination is made if all LEDs have been used (628). If not all LEDs have been used (NO at 628), the next LED is turned on (630) and the photodiode signals are recorded. The method continues until all LEDs have been used (YES at 628), at which point the method for the second optical cell ends (632).

After the optical measurements are complete, a pressure measurement is taken (634). A continuous sampling loop with three checkpoints determines if the conditions for termination of filtration are met. The three checkpoints are a determination of the transmembrane pressure (636), a determination of the cumulative fluorescence signal (correlated to biomass and gene copy numbers) (638), and total volume filtered (640), each with its own respective threshold. User-specified thresholds are also checked to not exceed device limitations. For example, the user pressure threshold cannot exceed the manufacturer's limit to ensure mechanical integrity and avoid loss of sample. Following in hierarchy are the fluorescence threshold and the volume threshold, respectively. When a threshold condition is met (YES at 636, 638, or 640), preservative is injected onto the filter membrane (642), and a determination is made whether all membrane filters have been used (644). If not all membrane filters have been used (NO at 644), the selector valve is incremented to the next membrane (646) and the process repeats. The process is repeated until all membranes have preserved sample. Once it is determined that all membrane filters have been used (YES at 644), the method ends (648).

Figure 7:
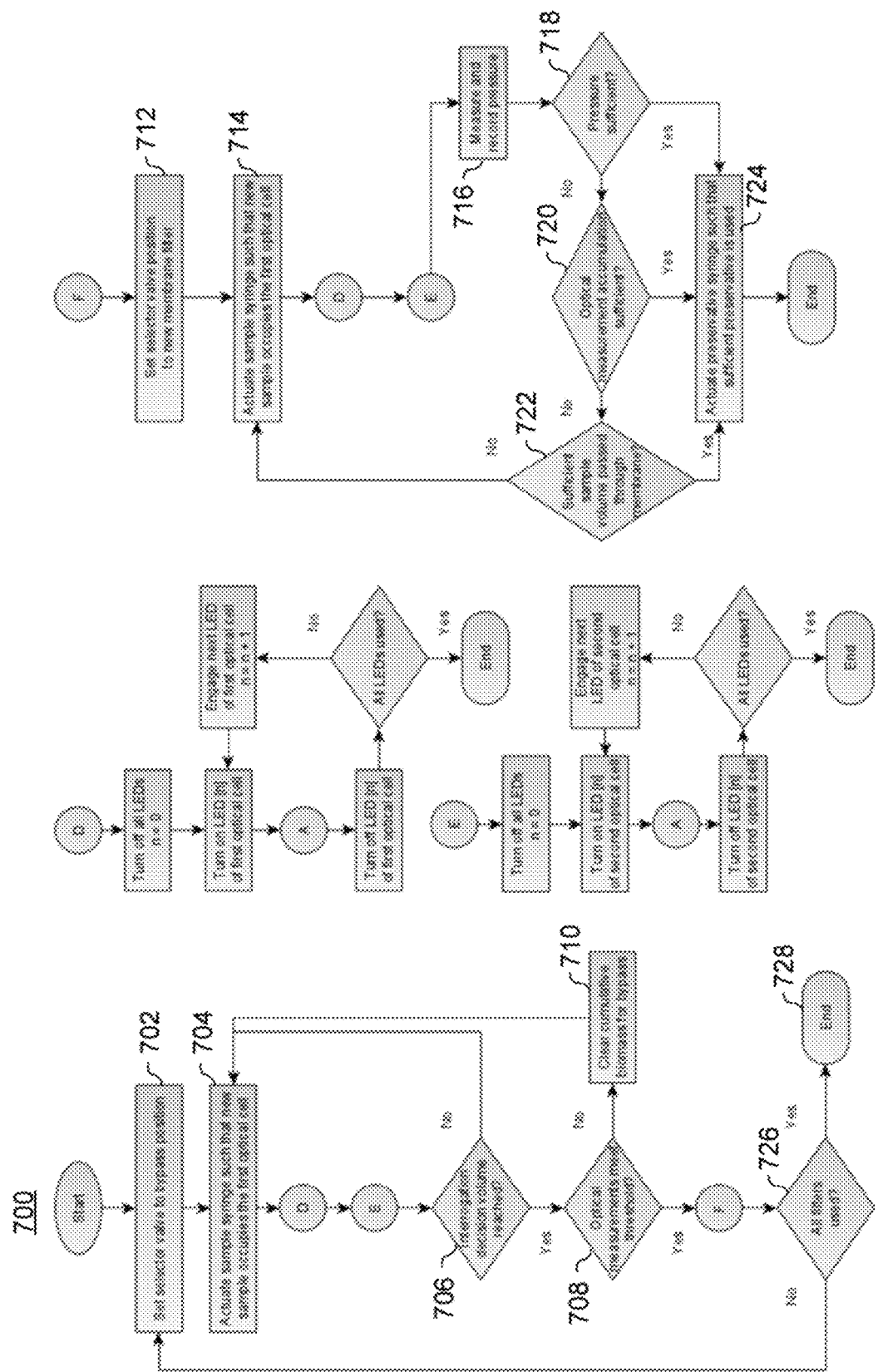
FIG. 7 shows a method for operating the microfluidic system utilizing a bypass channel.

FIG. 7 shows a method 700 for operating the microfluidic system utilizing the bypass channel. The process is similar to the method 600 described with reference to FIG. 6, except there are optical measurements acquired while a sample fluid stream is passed through the bypass channel in flow-thru mode. This permits continual monitoring of the local environment by pumping a sample stream through the first optical flow cell. The selector valve is set to the bypass position (702), and the sample syringe is actuated such that new sample is introduced to the first optical flow cell (704). Measurements are acquired at the first optical flow cell and the second optical flow cell at "D" and "E" as described with reference to FIG. 6. A determination is made whether an interrogation decision volume is reached (706). If the interrogation decision volume has not been reached (NO at 706), the method returns to actuating the sample syringe such that new sample is introduced to the first optical flow cell (704). If the interrogation decision volume has been reached (YES at 706), a determination is made whether optical measurements meet threshold (708). If the optical measurements do not meet the threshold (NO at 708), the cumulative biomass is cleared for bypass (710). When a critical optical threshold is detected (YES at 708) (e.g. cells per litre) to signify the presence of phytoplankton, the system can begin capturing on one of the filtration membranes for later genetic analysis using a method shown beginning at "F", which comprises setting the selector valve position to a new membrane filter (712), actuating the sample syringe such that new sample occupies the first optical cell (714), performing optical measurements using the first and second optical cells at "D" and "E" as previously described, measures and records pressure (716), and determines if the conditions for termination of filtration are met at (718), (720), and (722), wherein if a threshold condition is met (YES at 718, 720, or 722), preservative is injected onto the filter membrane (724). A determination is made whether all membrane filters have been used (726). If not all membrane filters have been used (NO at 726), the method returns to (702). If it is determined that all membrane filters have been used (YES at 726), the method ends (728). In the method, the user specifies the required interrogation volume that should be inspected and the cumulative optical threshold biomass within that volume before deciding to capture on the filter membranes. For example, the user may set a 1 L volume of sample to be optically interrogated to fulfill their target limit of detection for early HAB identification. The user may also set the optically detected cumulative biomass threshold to equate to a few cells per milliliter.

Figure 8:
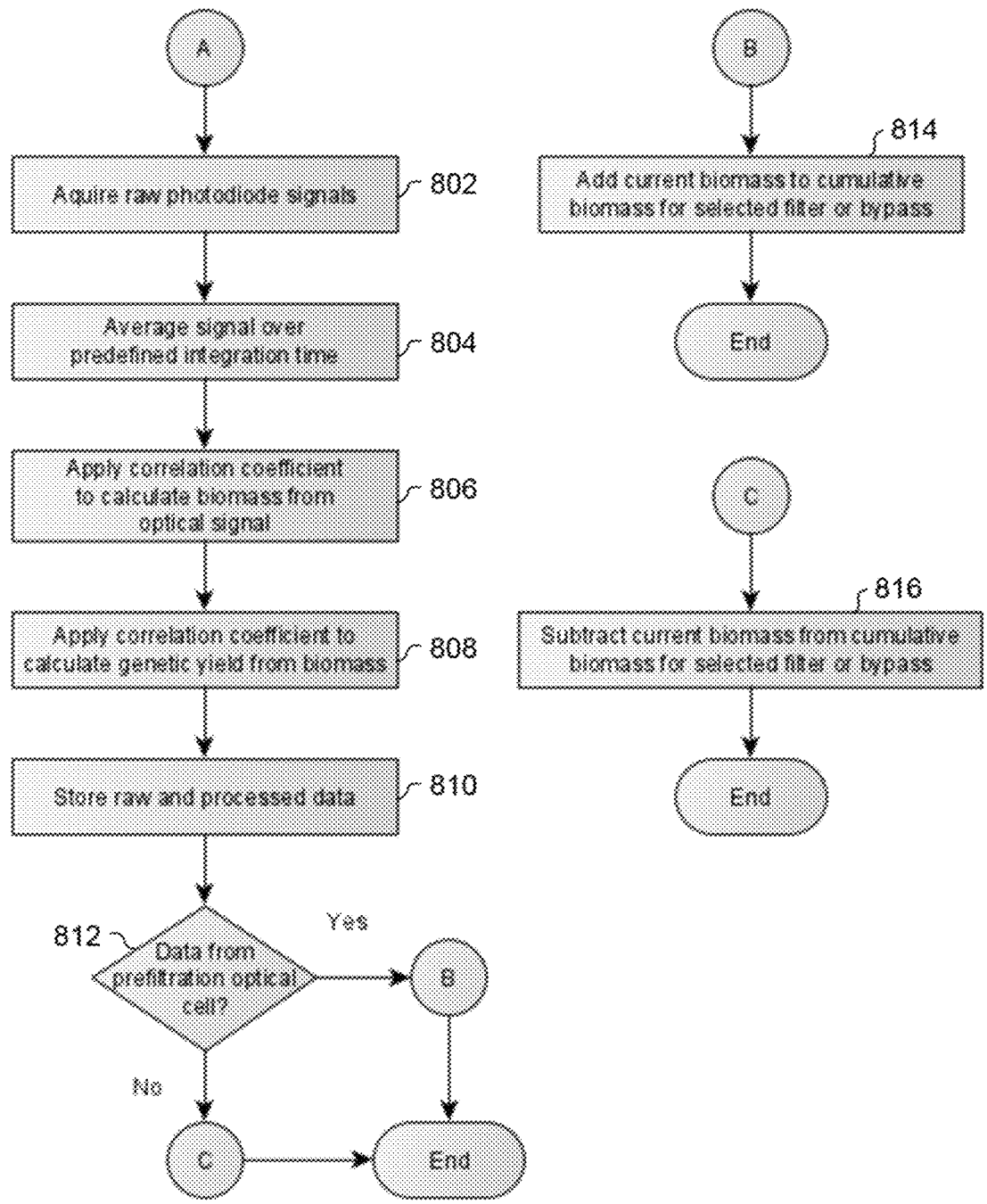
FIG. 8 shows a method for the analysis of absorbance and/or fluorescence data.

FIG. 8 shows a method for the analysis of absorbance and/or fluorescence data. The method occurs for one pigment target at a time, such that it is during the LED "on" phase of FIGS. 6 and 7. The "A" process begins with capturing several photodiode measurements (802) and integrating them for the predefined time (804). The averaged value of the optical signal is converted to an estimated biomass using a correlation coefficient (806). The estimated biomass is converted to an estimated genetic yield with another correlation coefficient (808). The raw and processed data is stored (810), and a determination is made whether data is from a prefiltration optical cell (812). The "B" process is for measurements acquired from the optical flow cell pre-filtration (YES at 812). As such, the detected biomass is added to the cumulative biomass for the selected filter membrane or bypass counter (814). Similarly, the acquired genetic yield is added to cumulative genetic capture on the membrane. The "C" process is for measurements from the optical flow cell after the membranes (NO at 812). As this is sample material that has not been captured or retained the measured biomass and/or genetic yield results are subtracted from the cumulative balance for the respective membrane (816). Optical data and associated coefficients are normalized to the cumulative fluid volume interrogated.

Figure 9:
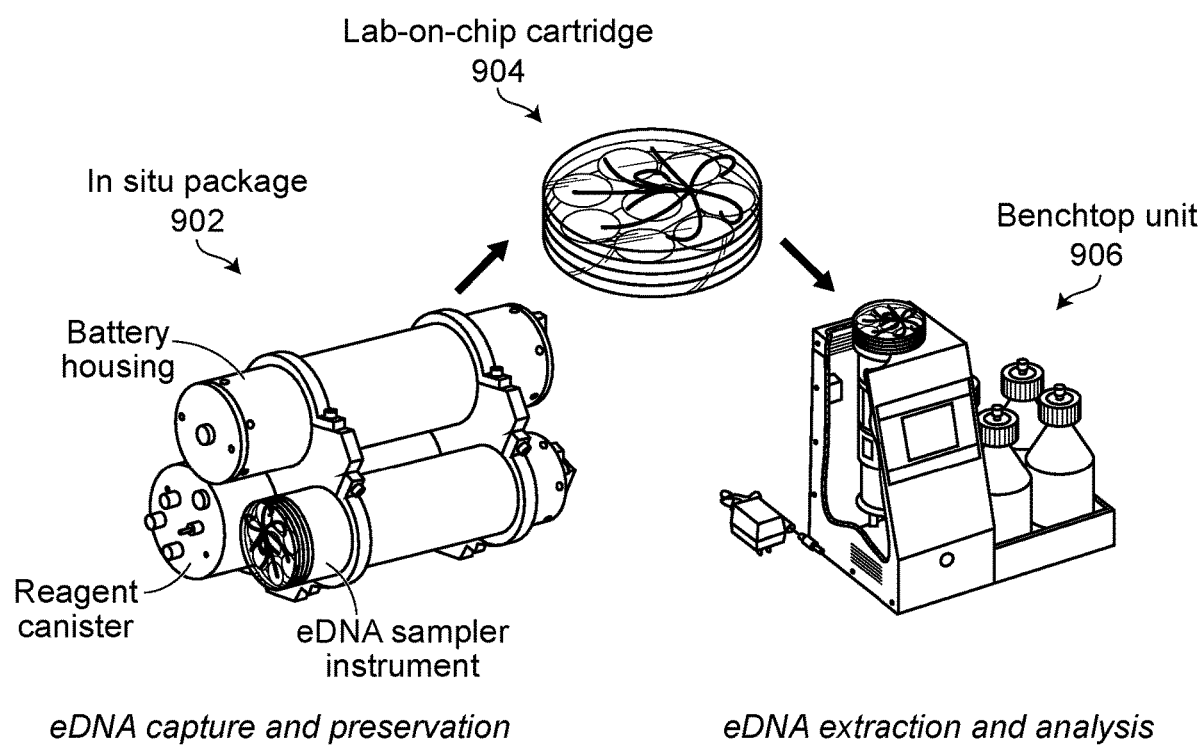
FIG. 9 shows integration of the microfluidic lab-on-chip device within an in situ package, a microfluidic lab-on-chip cartridge, and a benchtop unit.

FIG. 9 shows the integration of the microfluidic lab-on-chip device within an in situ package 902 (left), a microfluidic lab-on-chip cartridge 904 (center) and a benchtop unit 906 (right). The in situ package 902 contains a battery pack for energy, a reagent canister for preservative fluid and waste fluid, and an eDNA sampler instrument for eDNA capture and preservation. The eDNA sampler instrument comprises the microfluidic chip submerged in the environment to minimize dead-volume on the sample intake, as well as the various pumps, electronics and optical elements secured in a pressure casing or housing for controlling the chip. The microfluidic chip device contains integrated optical spectroscopy and sample filtration as described above to observe both pigment fluorescence and absorbance while microbes, algae and shed cells are captured on the membrane. Optical data are utilized and recorded over time by the eDNA sampler instrument to selectively capture target species, verify membrane integrity, quantify capture efficiency, and estimate accumulated biomass on the membrane surface. After the deployment, the microfluidic chip 904 may be transferred to a bench top instrument 906, which automates the process of eDNA extraction and analysis from the captured product on each membrane. This may include extraction of the eDNA template material from the microfluidic chip to Eppendorf tubes, strips or plates, for downstream analysis with qPCR instruments or other next generation sequencing equipment. In the example above, microfluidic device contains 2-ch. fluorescence and absorbance measurements for Chlorophyll A and Phycocyanin, with 8-membranes. Although a particular embodiment is described herein, it shall not limit the scope of the present invention that can be scaled to other quantities of filter membranes, as well as designed to observe alternative optical absorbance and/or fluorescence spectra.

Figure 10:
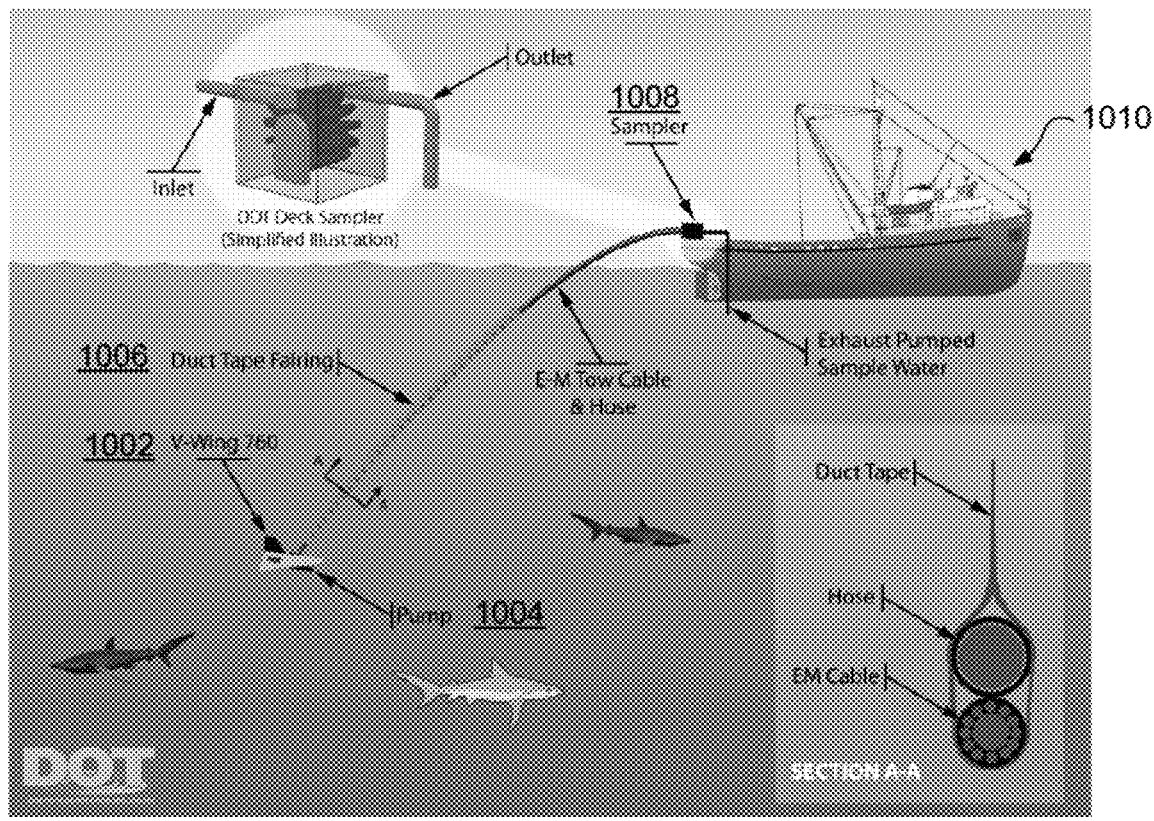
FIG. 10 shows an illustration of a configuration for pumping water up to a towing vessel for eDNA collection.

FIG. 10 shows an illustration of a configuration for pumping water up to a towing vessel for eDNA collection. FIG. 10 is an illustration of the use of a standard dihedral wing depressor 1002 to house a lift pump 1004 to take water from a relatively shallow depth (~10 meters) and pump it up to the towing vessel 1010 via a faired hose 1006. The tow body can be adjusted to a variety of depths and speeds allowing for easy sampling. The eDNA sampler instrument 1008 can collect samples on the surface of the vessel 1010 at a convenient location such as the aft deck as well as port or starboard of the ship, depending on the application. The system can collect many samples over the course of a day. On return to the dock the samples can be sent to a laboratory for processing. The samples can be processed looking for a variety of targeted DNA. An example of where this configuration might be used is to have a sampling system deployed on several vessels of opportunity (such as fishing vessels) along the coast of a given location. The target DNA can be a variety of fishing species including human predators such as sharks.

For performing downstream eDNA analysis, once RNAlater-treated filters are recovered from the device, they can be processed directly or stored a low temperature for short-term or long-term storage (1 week at 25° C., 1 month or more at 4° C., and long-term at −20° C. or −80°. The DNA can be extracted by the investigator's preferred method that accommodates samples preserved with RNAlater or by a recommended streamlined protocol provided with the eDNA sampler. Recovered DNA is prepared for characterization using one of several analytical techniques including quantitative PCR (qPCR), highly multiplexed amplicon sequencing of target-enriched DNA or metagenomics. The qPCR method for the detection of specific gene target is currently the method of choice for detecting rare eDNA target because of its broad dynamic range and low detection limit per sample.

For qPCR analysis, the eDNA extracted from the filters is quantified and its concentration noted. The qPCR assays are optimized for each target gene in order to ensure high amplification efficiency and low or preferably no amplification for No Template Controls (NTCs) in which the reaction is carried out without the target DNA. The quality of the NTCs depends on the design of primers that have low chance of annealing in the form of primer dimers or hairpin structures. Overall, a well-designed qPCR assay will have a 95% or greater amplification efficiency over a detection range of 7 orders of magnitude. The supported qPCR assays associated with the eDNA sampler will conform to the MIQE guidelines. The method may consist of easily adaptable modules that integrate the eDNA sampler with the downstream applications for the detection of target DNA sequences. For instance, *Alexandrium* is a genus of dinoflagellate that encompasses at least 30 distinct species, of which half are known to be HAB organisms. PCR primers can be designed to target any of these species individually, or the entire genus collectively. Standard primers exist that can amplify genes that are diagnostic of genus and species, but custom primers can be designed to target refined sets of species, or toxin genes more directly. The systems described herein can collect multiple samples, allowing the abundance of Alexandrium and other HAB species to be monitored spatially (e.g. through towed arrays or vertical profilers) or temporally from a fixed location. As a starting point, published qPCR assays for two target genes for *Alexandrium fundyensi*, the main culprit for Paralytic Shelfish Poisoning in North America and worldwide, have been adopted and tested. The selected targets are a gene involved in the production of saxitoxin and a taxonomic marker for *A. fundyensi*. In a qPCR assay calibrated with a target sequence standard of known copy numbers, the gene copy numbers are proportional to the density of the microorganism in the sample. This means the amount of DNA product generated is an indicator of the original environmental concentration of DNA. qPCR requires the use of short "primer" DNA sequences that bind to the desired target: these primers can be "standard" and in widespread use, or customized through a parallel process of primer design and validation that can target a gene of interest. The assays may be validated on a standard ABI vi7 instrument and on a portable compact thermocycler that can be deployed in the field (e.g. MyGo or other portable thermocycler) providing a closed process for the detection of HAB using the eDNA sampler.

Figure 11:
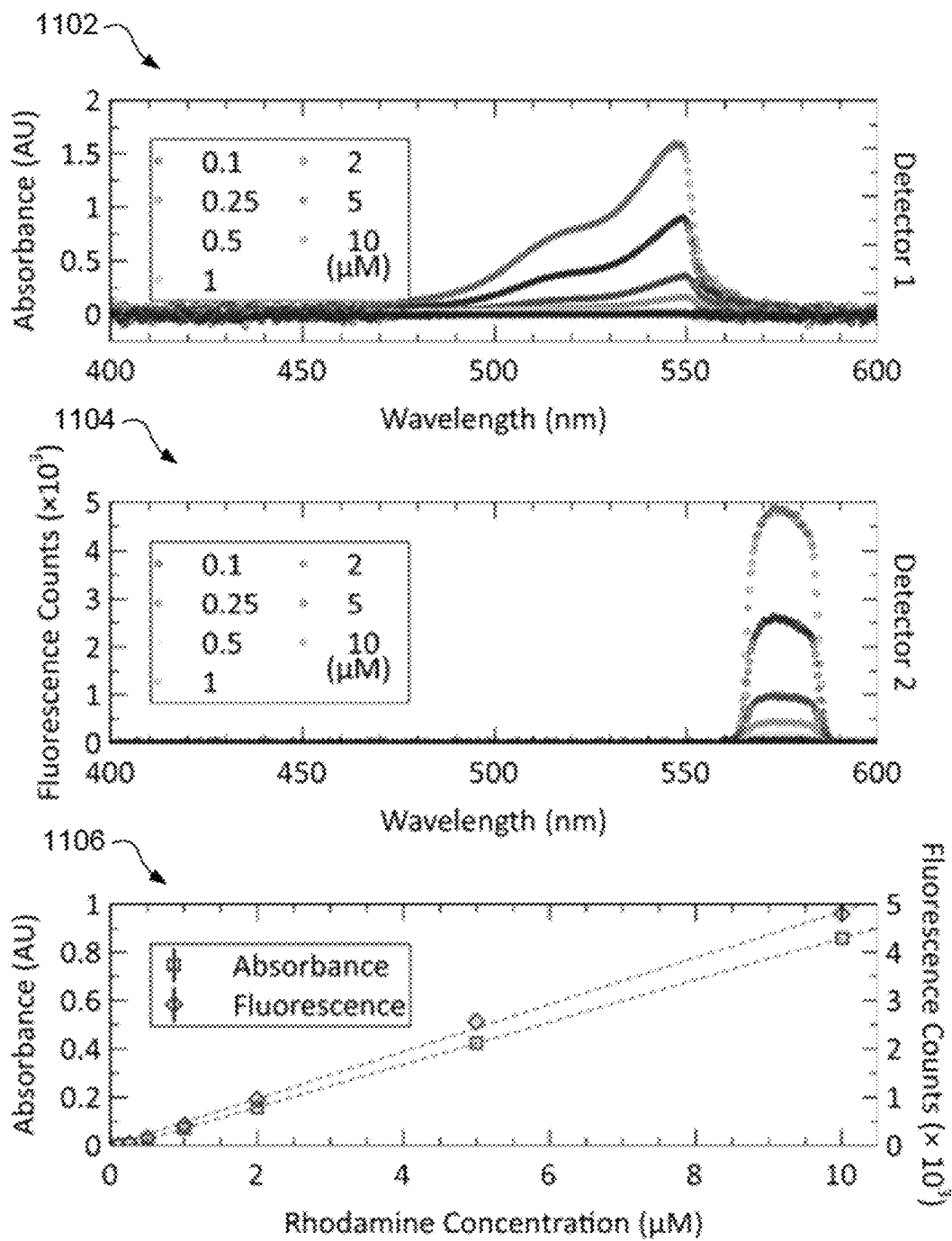
FIG. 11 shows a series of plots containing experimental data characterizing an optical cell used in the microfluidic chip.

FIG. 11 is a series of plots containing experimental data characterizing an optical cell used in the microfluidic chip. A microfluidic chip was fabricated containing an optical cell with both absorbance and fluorescence measurement capabilities. To assess measurement consistency and performance, the absorbance and fluorescence of seven samples of a fluorescent dye, rhodamine B, ranging from 0.1-10 μM were measured. The concentrations of each sample were: 0.1, 0.25, 0.5, 1, 2, 5, and 10 μM. First, a 2.5 g/L stock solution of rhodamine was prepared by diluting 0.5 g of rhodamine B (R6626 Sigma-Aldrich Canada, CAS 81-88-9, Lot # SHBL5990) with Milli-Q water to a total volume of 200 mL. Each sample was then prepared, from highest to lowest concentration, through serial dilutions.

Injection of fluids through the microfluidic chip was achieved using several components. A Vici Cheminert C65Z 10-port selector valve (Valco Instruments Co. Inc., Houston, TX) was used to pull from different samples without cross-contamination. Tubing connected each sample to a respective intake port on the valve. The output connected to the intake of an off-the-shelf Cavro XC syringe pump (Tecan Systems, San Jose, CA) which pumped at a consistent flow rate of 1.5 mL/min. The output of the syringe pump was connected to the input of the microfluidic chip using tubing.

An excitation light source was chosen to best match the absorbance spectra of rhodamine to produce ample fluorescence. Rhodamine excitation was achieved using a 521 nm LED. An excitation and an emission filter was used—mounted in front of the LED/detector respectively—to prevent overlapping of spectra. A 550 nm shortpass filter and a 578 nm bandpass filter with a 16 nm bandwidth were chosen as the excitation and emission filters. Two spectrometers, connected to a personal computer via USB, were used as detectors to acquire absorbance and fluorescence measurements.

Before each sample measurement, Milli-Q water was injected into the optical cell. The absorbance and fluorescence measured with Milli-Q in the cell served as a blank measurement for the successive sample. The absorbance and fluorescence of each sample concentration was measured in triplicate to assess measurement consistency. The following details the measurement procedure of any given concentration. First, 3 mL of Milli-Q was pumped through the chip. Upon stopped-flow, the readings of both spectrometers were recorded. Next, 3 mL of sample was pumped through the chip, and the same readings were recorded upon stopped-flow. This cycle was repeated three times to acquire three measurements of the sample.

Each sample was measured three independent times to assess measurement consistency. FIG. 11 demonstrates the experimental results obtained from these tests via a series of three plots. The top plot 1102 shows average absorbance vs. wavelength for each rhodamine sample. As expected, samples with a higher concentration of rhodamine dye consistently absorbed more. The middle plot 1104 shows average fluorescence vs. wavelength for each rhodamine sample. As expected, the samples that absorbed more (first plot) also fluoresced more (second plot). At these concentrations, the relationship between absorbance, fluorescence, and concentration is expected to be linear. This is shown by the bottom plot 1106 where absorbance/fluorescence are plotted against sample concentration. The average absorbance and fluorescence of each sample concentration was calculated over a 5 nm window in each case: 520-525 nm (abs.) and 570-575 nm (fl.). Error bars are used to demonstrate the associated uncertainty calculated for each data point. The small error bars demonstrate strong measurement consistency. Both data sets show strong linear relationships ($R^2 > 0.99$) as expected from a properly functioning absorbance/fluorescence detector.

Figure 12:
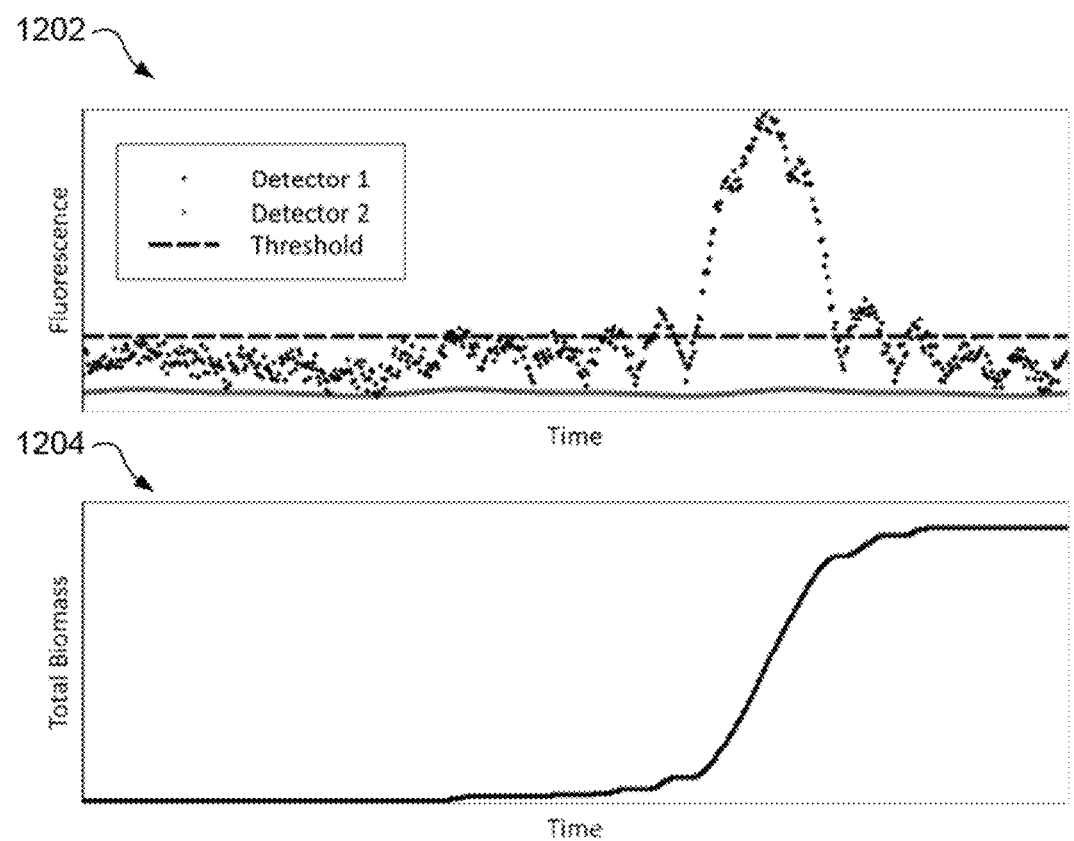
FIG. 12 shows a series of two concept plots that highlight the principle of taking eDNA sampler optical data and converting it cumulative biomass.

FIG. 12 is a series of two concept plots that highlight the principle of taking eDNA sampler optical data and converting it cumulative biomass. In the first plot 1202, top, the amount of fluorescence measured by the first fluorimeter is shown by black diamond-shaped data points. When the amount of fluorescence measured by the fluorimeter is below the detection limit threshold value—marked as a black dashed line—data is not counted as it is below the signal-to-noise level. When the measured fluorescence of a sample exceeds the threshold, the signal is counted toward the total or cumulative collected biomass sample. The grey triangle-shaped data points in the top plot represent measurements by the second fluorometer. Their small amplitude conveys the expectation that minimal fluorescing species pass through the membrane. Minor fluctuations are shown which simulate electrical/optical noise. In the second plot 1204, bottom, the total amount of collected biomass is shown over time. Initially upon sensor deployment, there is no collected biomass on any membrane and the total is zero. Whenever the first fluorometer detects a sufficiently high amount of fluorescence, biomass is collected onto the currently selected filter and the total amount of collected biomass increases. Each filter membrane will have its own cumulative biomass and gene copy estimate, along with the total volume of fluid filtered. The "gene copy number per mL" information is used as input for downstream qPCR protocols.

In accordance with one embodiment described herein the microfluidic system is a microfluidic chip that is fabricated from four layers of 6 mm thick transparent polymethyl (methacrylate) (PMMA), two layers of 3 mm thick opaque black PMMA a set of permanent magnets, eight filter membranes, and eight accompanying O-rings. The machining was carried out on an LPKF S103 Micromill and a 50 W Epilog Mini Helix Laser Cutter. Chip bonding was done using a chloroform vapor exposure and an LPKF Multipress II. The microfluidic chip may be made in three distinct phases, each comprised of several sub-steps.

Phase One: Creating the Inlays

A sheet of 6 mm thick clear transparent PMMA is set on the bed of the micromill, where holes for fiducial alignment and 3 mm deep cavities for the inlaid pieces are milled. The 3 mm thick sheet of opaque black PMMA is set on the laser cutter, where the two inlaid pieces are cut out. The two black inserts are then vapor treated with chloroform for 45 seconds. This is done by suspending the pieces above a chloroform bath heated to 35 C in a confined space. The treated inserts are then manually pressed into their respective cavities in the clear sheet, and then pressed in the multipress at 116 C using 430 kPa of pressure for 2 hours. The heat is then turned off and the sheet is allowed to cool to room temperature under pressure. The now uniform sheet is then removed from the press and set back on the micromill bed for phase two.

Phase Two: Milling the Features

All of the fluidic ports and channels are created using the LPKF S103 Micromill. The now inlaid sheet of clear PMMA is set on the mill bed and planed down by 250 μm to ensure a flat and uniform surface. The previously drilled fiducials are used for alignment and the channels and features are then milled. The channels are milled to be both 400-600 μm deep and wide using a 400-600 μm end mill, with size dependent on user requirements. The prisms are created using a 45-degree cutter and milled to be at least the depth and width of the channel. Shallow recesses for the filter membranes and deeper recesses for the permanent magnets are milled to ensure proper retention and placement of the membranes. Circular grooves are created to provide a seat for the O-rings. After all the features are milled on both sides of the inlaid sheet, the sheet is then returned to the laser cutter for phase three.

Phase Three: Bonding the Chip

The laser cutter is used to cut out the four now detailed discs out of the inlaid sheet. The discs are then set on a hot plate at 85 C for at least three hours to prevent micro fractures from occurring along the laser cut edges. Each disc is then lightly sanded and thoroughly cleaned using water, soap, isopropyl alcohol, and compressed air. In the same process as previously described, the four discs are then vapor treated with chloroform for 45 seconds. They are then removed from chloroform bath and the permanent magnets are inserted into their assigned recesses. Next, the top two layers are manually pressed together, and the bottom two layers are manually pressed together. Each set is then pressed in the multipress at 85 C using a pressure of 6.25 MPa for 2.5 hours. The two chip halves are then removed, and the filter membranes and O-rings are carefully placed in their respective recesses. The two halves are then brought together where they are held in contact by the force of the embedded magnets.

It would be appreciated by one of ordinary skill in the art that the system and components shown in the figures may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as described herein.

The invention claimed is:

1. A microfluidic system, comprising:
   an environmental sample inlet port;
   a preservative reagent inlet port;
   a waste outlet port;
   one or more discrete filter membranes for particle concentration;
   at least one fluid access port that permits control of a sample fluid stream through a selected filter membrane of the one or more discrete filter membranes;
   at least one optical flow cell that enables at least one of light microscopy, fluorescence spectroscopy, light attenuation measurements, and scattered light intensity measurements, situated before the one or more discrete filter membranes to interrogate the sample fluid stream;
   at least one bypass channel to enable disposal of the sample fluid stream and avoid capturing suspended microbes and/or particles on the one or more discrete filter membranes;
   a photodetector positioned at the at least one optical flow cell and configured to measure absorbance or fluorescence changes in the sample fluid stream; and
   a processing unit configured to receive data from the photodetector and analyze the absorbance or fluorescence changes to enable intelligent fluid routing to the one or more discrete filter membranes and/or the at least one bypass channel.

2. The microfluidic system of claim 1, wherein the microfluidic system comprises a microfluidic chip having a plurality of layers, comprising:
   an upper layer comprising the environmental sample inlet port, the preservative reagent inlet port, the waste outlet port, and in fluid communication with at least one intermediate layer;
   an intermediate layer in fluidic communication with the one or more discrete filter membranes; and
   a lower layer in fluid communication with the intermediate layer, incorporating the at least one fluid access port, and the at least one optical flow cell in optical communication with an instrumentation housing.

3. The microfluidic system of claim 1, wherein the at least one optical flow cell comprises at least one of an absorbance measurement channel and a fluorescence measurement chamber.

4. The microfluidic system of claim 3, wherein the photodetector detects chlorophyll and/or phycocyanin absorbance or fluorescence changes.

5. The microfluidic system of claim 1, wherein optical measurements are used to determine redirection of sample away from the one or more discrete filter membranes via the at least one bypass channel.

6. The microfluidic system of claim 1, wherein optical measurements are used to determine whether sufficient gene copy numbers per liter filtered have been collected on a targeted filter membrane of the one or more discrete filter membranes by estimating biomass through at least one correlation factor.

7. The microfluidic system of claim 6, further comprising a pressure sensor, and wherein pressure measurements are used to determine sufficient sample concentration and/or biomass collection on the targeted filter membrane, and wherein sample fluid volume filtered through each filter membrane of the one or more discrete filter membranes is tracked and recorded to determine gene copy numbers per liter.

8. The microfluidic system of claim 1, comprising a plurality of discrete filter membranes, wherein a branched multiplexing channel links the environment sample inlet port to the plurality of discrete filter membranes; and fluid flow through a respective filter membrane is enabled by a selector valve on the outlet side of each filter membrane, enabling selective capture of particles and microbes in the sample fluid stream on a desired filter membrane.

9. The microfluidic system of claim 1, wherein a meandering channel extends behind the one or more discrete filter membranes for providing volume capacity to avoid preservative from entering the waste outlet port.

10. The microfluidic system of claim 1, wherein the processing unit is configured to receive data from the photodetector for analyzing the sample's fluorescence spectral data to determine the presence of phytoplankton and cyanobacteria.

11. The microfluidic system of claim 1, further comprising multiple light emitting diode sources, configured to be activated sequentially to identify and record at least one of fluorescence and absorbance spectral signatures.

12. The microfluidic system of claim 1, wherein the environmental sample inlet port is configured to receive the sample fluid stream from a lift pump on a towed-body to enable capture of eDNA samples topside on a ship-based system, while the collection point is submerged.

13. The microfluidic system of claim 2, further comprising a magnetic retention of the microfluidic chip layers to enable rapid membrane removal and/or insertion.

14. The microfluidic system of claim 1, further comprising a second optical flow cell situated after the one or more discrete filter membranes for acquiring optical data of the permeate or post-filtration.

15. The microfluidic system of claim 14, wherein signals from a first optical flow cell of the at least one optical flow cell are compared to signals from the second optical flow cell to detect capture efficiency; and wherein the signals from the first and second optical flow cells, before and after filtration, enable detection of filter membrane failures of the one or more discrete filter membranes, and quantification of membrane capture efficiency as relates to pore-size and particle composition in the sample fluid stream, and wherein the microfluidic system further comprises a memory storing non-transitory computer-readable instructions that, when executed by the processing unit causes the processing unit to calibrate the first optical flow cell data to the second optical flow cell data using the at least one bypass channel.

16. The microfluidic system of claim 1, wherein the at least one optical flow cell comprises measurement ports at multiple angles for particle sizing.

17. The microfluidic system of claim 1, wherein at least one of a fluorescence signal threshold and an attenuation signal threshold is used to trigger capture on a filter membrane of the one or more discrete filter membranes with appropriate time stamp.

18. The microfluidic system of claim 17, wherein time-series fluorescence and absorbance spectra are used to determine sample concentration, or gene copy numbers per liter filtered, collected on a targeted filter membrane of the one or more discrete filter membranes by estimating biomass through at least one correlation factor.

19. The microfluidic system of claim 17, wherein the microfluidic system is configured to interface with a benchtop apparatus for subsequent eDNA extraction and analysis procedures.

20. The microfluidic system of claim 19, wherein the at least one optical flow cells are used to capture eluted pigment spectral data during DNA extraction to correlate to biomass captured.

21. The microfluidic system of claim 19, wherein the downstream analysis takes the DNA product or template to determine the presence of genes that are characteristic of certain species, including toxin genes.

22. The microfluidic system of claim 7, wherein a volume threshold, a pressure threshold, an optical threshold, and/or any combination thereof are user-specified to determine when to initiate and terminate the filtration of the sample fluid stream on a particular filter membrane of the one or more discrete filter membranes.

23. A method, comprising:
deploying the microfluidic system of claim 1 on a submersible instrument;
collecting a sample on the one or more discrete filter membranes;
conveying acquired data to operators via at least one of memory mode or wireless linkages;
retrieving the microfluidic system upon collecting sufficient biomass; and
connecting the microfluidic system to a benchtop stand-alone system for performing eDNA extraction procedures.

24. The method of claim 23, wherein optical data is shared with a deployment platform's autonomy framework for intelligent sampling that can be coordinated with the platform's georeferenced location, and further comprising performing adaptive sampling where the real-time measured optical data and a user-specified threshold are communicated to an autonomous water craft or vehicle that performs navigation and localization for automated eDNA water collection, including searching for the absence or presence of specific spectral signatures such as increases in phytoplankton.

* * * * *